United States Patent [19]

Eakin et al.

[11] Patent Number: 4,670,592

[45] Date of Patent: Jun. 2, 1987

[54] BISBIGUANIDE COMPOUNDS

[75] Inventors: Murdoch A. Eakin, Macclesfield; Philip N. Edwards, Bramhall; Michael S. Large, Congleton, all of England

[73] Assignee: Imperial Chemical Industries PLC, London, England

[21] Appl. No.: 607,702

[22] Filed: May 7, 1984

[30] Foreign Application Priority Data

May 9, 1983 [GB] United Kingdom ............... 8312663

[51] Int. Cl.$^4$ ........................................... C07C 129/16
[52] U.S. Cl. ................................. 564/234; 564/163; 564/192; 564/233; 564/235; 260/239 A; 260/239 B; 260/243.3; 260/244.4; 260/501.14; 546/186; 546/191; 546/193; 546/194; 546/208; 546/231; 548/523; 548/569; 544/86; 544/111; 544/121; 544/129; 544/141; 544/357; 544/359; 544/360; 544/372; 544/402; 558/411; 560/34
[58] Field of Search ............... 564/233, 234, 235, 163, 564/192; 424/326; 260/239 B, 239 A, 243.3, 244.4; 544/86, 111, 121, 129, 141, 357, 359, 360, 372, 402; 546/186, 191, 193, 194, 208, 231; 548/523, 569; 514/635; 560/34; 558/411

[56] References Cited

U.S. PATENT DOCUMENTS 3,468,898  9/1969  Cutler et al. .................. 564/233

FOREIGN PATENT DOCUMENTS 705838  3/1954  United Kingdom .
1095902 12/1967  United Kingdom .

Primary Examiner—James H. Reamer
Assistant Examiner—L. Hendriksen
Attorney, Agent, or Firm—Cushman, Darby & Cushman

[57] ABSTRACT

A bisbiguanide compound of the formula:

$$R^1R^2N.C(:NR^6)NH.C(:NH)NH.CH_2X-$$
$$-(CH_2)_3NH.C(:NH)NH.C(:NR^7)NR^3R^4 \quad V$$

or a tautomer thereof, wherein $R^1$, $R^2$, $R^3$ and $R^4$ which may be the same or different, are each hydrogen, a 1-16C alkyl radical, a 2-16C alkoxyalkyl radical, a 3-12C cycloalkyl radical, a (3-12C cycloalkyl)-(1-4C alkyl) radical, or an optionally substituted phenyl or phenyl(1-4C alkyl) radical, or $R^1$ and $R^2$ and the nitrogen atom to which they are attached, or $R^3$ and $R^4$ and the nitrogen atom to which they are attached, which may be the same or different, are each a 1-azetidinyl, 1-pyrrolidinyl, piperidino, hexamethyleneimino, heptamethyleneimino, morpholino or 4-(1-8C alkanoyl)-1-piperazinyl radical each of which may bear 1-3C alkyl substituents; each of $R^6$ and $R^7$, which may be the same or different, is hydrogen or a 1-8C alkyl radical; and X is a substituted ethylene or ethylidene radical of the formula:

$$-CH_2CH(YR^5)- \quad VI$$

or $$-CH(CH_2YR^5)- \quad VII$$

reading from left to right in formula V above, wherein Y is an oxygen or sulphur atom and $R^5$ is a 1-16C alkyl, 3-12C cycloalkyl, (3-12C cycloalkyl)-(1-4C alkyl), optionally substituted phenyl or optionally substituted phenyl(1-4C alkyl) radical, and the acid addition salts thereof, processes for their manufacture and antibacterial and antifungal compositions and methods using said compounds.

5 Claims, No Drawings

BISBIGUANIDE COMPOUNDS

This invention relates to bisbiguanide derivatives, and in particular to bisbiguanides which possess antibacterial properties.

Certain bisbiguanides are well-known as anti-bacterial agents, particularly antiseptic, agents. For example, in United Kingdom patent specification No. 705,838 there are disclosed and claimed bisbiguanides of the general formula:

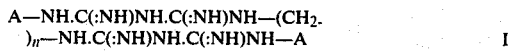
A—NH.C(:NH)NH.C(:NH)NH—(CH$_2$.)$_n$—NH.C(:NH)NH.C(:NH)NH—A  I wherein A stands for a phenyl radical, which is substituted by alkyl, alkoxy, nitro or halogen, and wherein the two A's may be the same or different, and wherein n is an integer from 3 to 9 inclusive, and wherein the polymethylene chain may be interrupted by oxygen atoms and/or by aromatic nuclei. The compounds are said to be useful as bactericides; for example, those of the formula:

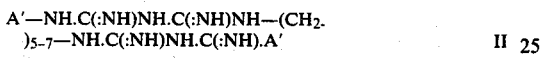
A'—NH.C(:NH)NH.C(:NH)NH—(CH$_2$.)$_{5-7}$—NH.C(:NH)NH.C(:NH).A'  II wherein A' stands for a halogen substituted phenyl radical possess very high antibacterial activity when tested in vitro against the organisms *Streptococcus haemolyticus, Staphylococcus aureus, Bacillus coli, Clostridium welchii* and *Pseudomonas pyocyanea*.

Similarly, in United Kingdom patent specification No. 1,095,902 there is disclosed and claimed a broad group of bisguanides and bisbiguanides which includes inter alia compounds of the formula:

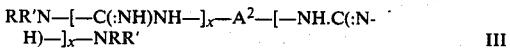
RR'N—[—C(:NH)NH—]$_x$—A$^2$—[—NH.C(:NH)—]$_x$—NRR'  III wherein A$^2$ stands for an alkylene radical of 2 12 carbon atoms having the valency bonds attached to different carbon atoms, or for a group of the formula:

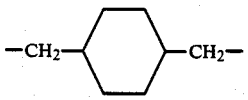
IV

R stands for an alkyl radical of 6 to 16 carbon atoms, R' stands for hydrogen and x stands for 1 or 2. The bisguanides and bisbiguanides are said to have particular usefulness as plant fungicides and bactericides.

According to the present invention there is provided a bisbiguanide compound of the formula:

R$^1$R$^2$N.C(:NR$^6$)NH.C(:NH)NH.CH$_2$X—(CH$_2$)$_3$NH.C(:NH)NH.C(:NR$^7$)NR$^3$R$^4$  V or a tautomer thereof, wherein R$^1$, R$^2$, R$^3$ and R$^4$ which may be the same or different, are each hydrogen, a 1–16C alkyl radical, a 2–16C alkoxyalkyl radical, a 3–12C cycloalkyl radical, a (3–12C cycloalkyl)-(1–4C alkyl) radical, an optionally substituted phenyl or phenyl(1–4C alkyl) radical, or R$^1$ and R$^2$ and the nitrogen atom to which they are attached, or R$^3$ and R$^4$ and the nitrogen atom to which they are attached, which may be the same or different, are each a 1-azetidinyl, 1-pyrrolidinyl, piperidino, hexamethyleneimino, heptamethyleneimino, morrpholino or 4-(1–8C alkanoyl)-1-piperazinyl radical each of which may bear 1–3 C alkyl substituents; each of R$^6$ and R$^7$, which may be the same or different, is hydrogen or a 1–8C alkyl radical; and X is a substituted ethylene or ethylidene radical of the formula:

—CH$_2$CH(YR$^5$)—   VI or

—CH(CH$_2$YR$^5$)—   VII reading from left to right in formula V above, wherein Y is an oxygen or sulphur atom and R$^5$ is a 1–16C alkyl, 3–12C cycloalkyl, (3–12C cycloalkyl)-(1–4C alkyl), optionally substituted phenyl or optionally substituted phenyl(1–4C alkyl) radical, and the acid addition salts thereof.

Each of R$^1$, R$^2$, R$^3$, R$^4$, and R$^5$ may be, for example, a methyl, ethyl, n-propyl, isopropyl, n-butyl, isobutyl, sec-butyl, tert-butyl, pentyl, neopentyl, octyl, 2-ethylhexyl, dodecyl, hexadecyl, cyclobutyl, cyclopentyl, cyclohexyl, cycloheptyl, cyclopentylmethyl or cyclohexylmethyl radical, particularly the methylhexyl, n-hexyl and cyclohexyl radicals.

Each of R$^6$ and R$^7$ may be, for example, a methyl, ethyl, n-propyl, isopropyl, n-butyl, isobutyl, sec-butyl, tert-butyl, pentyl, neopentyl or octyl radical.

When any of R$^1$, R$^2$, R$^3$, R$^4$, and R$^5$ is an optionally substituted phenylalkyl radical, it is preferably a benzyl, α-methylbenzyl, α-ethylbenzyl or phenethyl radical, and suitable optional substituents in the phenyl ring thereof or in R$^1$, R$^2$, R$^3$, R$^4$ and R$^5$ when any of them is a phenyl radical are, for example, halogen atoms, for example chlorine, bromine, iodine or fluorine atoms, amino, carbamoyl, cyano, hydroxy, nitro and trifluoromethyl radicals, 1–6C alkyl, alkoxy, alkanoyl, alkylamino and alkanoylamino radicals and 2–6C alkoxycarbonyl and dialkylamino radicals. Suitable such radicals are, for example, methyl, ethyl, propyl, butyl, pentyl, hexyl, methoxy, ethoxy, propoxy, acetamido, propionamido, butramido, methylamino, ethylamino, propylamino, acetyl, propionyl, butyryl, methoxycarbonyl, ethoxycarbonyl, dimethylamino and diethylamino radicals. Up to five such substituents may be present, but mono- and di-substituted phenyl rings are preferred, and especially mono-substituted rings.

Thus, further suitable value for R$^1$, R$^2$, R$^3$, R$^4$ and R$^5$ are, for example, 2-, 3- and 4-chlorophenyl, 2-, 3- and 4-bromophenyl, 2-, 3- and 4-fluorophenyl, 2,3-, 2,4-, 2,5-, 2,6-, 3,4- and 3,5-dichlorophenyl, 2-chloro-4fluorophenyl, 2-, 3- and 4-methylphenyl, 2,3-, 2,4-, 2,5-, 2,6-, 3,4- and 3,5-dimethylphenyl, 2-, 3- and 4-methoxyphenyl, 2-, 3- and 4-acetylphenyl, 2-, 3- and 4-methylaminophenyl, 2-, 3and 4-acetamidophenyl, 2-, 3- and 4-methoxycarbonylphenyl, 2-, 3-and 4-dimethylaminophenyl, 2-, 3- and 4-nitrophenyl, 2-, 3- and 4-chlorobenzyl, 2-, 3- and 4-bromobenzyl, 2-, 3- and 4-fluorobenzyl, 2,3-, 2,4-, 2,5-, 2,6-, 3,4- and 3,5-dichlorobenzyl, 2-chloro-4-fluorobenzyl, 2-, 3- and 4-methylbenzyl, 2,3-, 2,4-, 2,5-, 2,6-, 3,4- and 3,5-dimethylbenzyl, 2-, 3- and 4-methoxybenzyl, 2-, 3- and 4-acetylbenzyl, 2-, 3- and 4-methylaminobenzyl, 2-, 3- and 4-acetamidobenzyl, 2-, 3- and 4-methoxycarbonylbenzyl, 2, 3- and 4-dimethylaminobenzyl, 2-, 3- and 4-nitrobenzyl, 2-, 3- and 4-chloro-α-methylbenzyl, 2-, 3- and 4- nitrobenzyl, 2-, 3- and 4-chlorophenethyl and bis-(2-, 3- and 4-chlorophenyl)methyl radicals.

When one or more of $R^1$, $R^2$, $R^3$ and $R^4$ is an alkoxyalkyl radical, it may be, for example, a 2-methoxyethyl, 3-dodecyloxypropyl, 6-hexyloxyhexyl, 2-tetra-decyloxyethyl or 15-methoxypentadecyl radical.

When $R^1$ and $R^2$, and $R^3$ and $R^4$, together with the nitrogen atoms to which they are attached, form a heterocyclic radical, preferred such radicals are the 1-pyrrolidinyl and piperidino radicals.

The acid-addition salts of the invention may be derived from an inorganic or organic acid. In most circumstances it is preferable that the salts be derived from an acid which affords an anion which is suitable for human usage, for example a pharmaceutically-acceptable anion. Examples of such acids are hydrochloric, hydrobromic, phosphoric, sulphuric, acetic, D-gluconic, 2-pyrrolidino-5-carboxylic, methanesulphonic, carbonic, lactic and glutamic acids.

Particular preferred bisbiguanide compounds of this invention are 2-(benzyloxymethyl)pentane-1,5-bis(5-hexylbiguanide), 2-(phenylthiomethyl)pentane-1,5-bis(5-phenethylbiguanide), 2-(decylthiomethyl)pentane-1,5-bis(5-isopropylbiguanide), 2-(decylthiomethyl)pentane-1,5-bis(5,5-diethylbiguanide), 3-(phenylthio)hexane-1,6-bis(5-hexylbiguanide), 3-(phenylthio)hexane-1,6-bis(5-cyclohexylbiguanide), 3-(benzylthio)hexane-1,6-bis(5-hexylbiguanide) and 3-(benzylthio)hexane-1,6-bis(5-cyclohexylbiguanide), and their dihydrochlorides.

According to a further feature of the invention there is provided a process for the manufacture of the biguanide compounds of the formula V wherein $R^6$ and $R^7$ are each hydrogen, which comprises reacting a biscyanoguanidine of the formula:

NC.NH.C(:NH)NH.CH$_2$X(CH$_2$)$_3$NH.C(:NH)NH.-CN      VIII with an amine $R^1R^2NH$, or with two different amines $R^1R^2NH$ and $R^3R^4NH$, in the form of an acid addition salt thereof, wherein X, $R^1$, $R^2$, $R^3$ and $R^4$ have the meanings stated above, at a temperature of 100° C. to 170° C.

A suitable amine salt is, for example, the hydrochloride. The reactants are heated together until the reaction is complete. The reaction proceeds fastest at higher temperatures, but if thermal stability is a problem, the reaction should be carried out at lower temperature for a longer period. The reactants are most conveniently melted together in the absence of a solvent, but if desired an inert solvent such as 2-methoxyethanol, 2-ethoxyethanol, nitrobenzene, sulpholane, isopropanol, n-butanol, ethylene glycol dimethyl ether or water, or a mixture of such solvents, may be used.

The bis-cyanoguanidine of the formula VIII wherein X is a substituted ethylene (VI) or ethylidine (VII) radical as defined above, which may be used as the starting material in the above process, may be manufactured from known starting materials 2-hexenedinitrile and 2-methyleneglutaronitrile respectively by reaction with a compound $R^5YH$, and a strong base to form a substituted dinitrile of the formula IX which is reduced, for example with hydrogen and Raney nickel or with borane in dimethyl sulphide to the corresponding diamine X, and the diamine X, in the form of an acid-addition salt, conveniently the dihydrochloride, is reacted with sodium dicyanamide to form the required starting material VIII.

NC.X(CH$_2$)$_2$CN $\longrightarrow$ NH$_2$CH$_2$X(CH$_2$)$_3$NH$_2$ $\longrightarrow$ VIII

IX                         X

According to a further feature of the invention there is provided a process for the manufacture of the compounds of the invention which comprises reacting a diamine of the formula NH$_2$CH$_2$X(CH$_2$)$_3$NH$_2$ (X) in the form of an acid addition salt, with a cyanoguanidine of the formula:

$R^1R^2N.C(:NR^6)NH.CN$      XI or with a cyanoguanidine of the formula XI and a cyanoguanidine of the formula:

$R^3R^4N.C(:NR^7)NH.CN$      XII and wherein X, $R^1$, $R^2$, $R^3$, $R^4$, $R^6$ and $R^7$ have the meanings stated above, at a temperature of 100° to 170° C.

A suitable salt of the diamine is, for example, the dihydrochloride. The reactants are heated together until the reaction is complete. The reaction proceeds fastest at higher temperature, but if thermal stability is a problem, the reaction should be carried out at lower temperature over a longer period. If a melt can be formed at those temperatures the reactants are conveniently melted together in the absence of a solvent. If not, or alternatively, the reactants are heated together in a suitable inert solvent, for example those mentioned above.

The acid-addition salts of the invention are obtained by conventional means.

The cyanoguanidines of the formulae XI and XII wherein $R^6$ and $R^7$ are hydrogen, which may be used as starting materials in the above process may be obtained by reacting sodium dicyanamide with an appropriate amine $R^1R^2NH$ or $R^3R^4NH$, in the form of an acid-addition salt, conveniently the dihydrochloride, in a suitable inert solvent.

The cyanoguanidines of the formulae XI and XII wherein $R^6$ and $R^7$ are other than hydrogen, which may be used as starting materials in the above process, may be obtained by reacting a dialkyl (cyanoimido)dithiocarbonate, for example dimethyl (cyanoimido)dithiocarbonate, $(MeS)_2C:N.CN$, with appropriate amines $R^1R^2NH$ and $R^6NH_2$ or $R^3R^4NH$ and $R^7NH_2$.

The antibacterial activity of the compounds of the invention has been measured by the well-known minimum inhibitory concentration (MIC) test. Neat or diluted broth cultures of eight Gram positive organisms (*Streptococcus pyogenes, S. faecalis*, 3 strains of *Staphylococcus aureus, Listeria monocytogenes, Streptococcus mutans, S. sanguis*), *Candida albicans* and fourteen Gram negative organisms (4 strains of *Escherichia coli, Salmonella dublin, Klebsiella aerogenes, K. pneumoniae, E cloacae, Serratia marcescens, Proteus vulgaris, P. mirabilis* and 3 strains of *Pseudomonas aeruginosa*) were inoculated by means of an automatic microtitre inoculator on the surface of nutrient agar plates containing two-fold or five-fold dilutions of a test compound. After incubation overnight at 37° C., the MIC's of the test compound are read. The geometric mean MIC's for the eight Gram positive organisms and Candida, and 14 Gram negative organisms are then calculated for each test compound.

Depending upon its precise chemical structure, a compound of the invention has a mean MIC within the range 1-12 µg./ml. in agar against the 8 Gram positive organisms and Candida, and 20-250 µg./ml. in agar against the 14 Gram negative organisms.

The preferred compounds of the invention have an acute $LD_{50}$ within the accepted limits for compounds used topically, are of low irritancy in the Draize test on intact rabbit skin, are negative in the Ames test for mutagenicity, and are non-sensitizing in the Magnusson and Kligman contact sensitivity test in guinea pigs.

Because of their antibacterial and/or antifungal properties, the compounds of the invention are useful for many purposes, for example:

(a) in medical and veterinary practice for the disinfection of wounds, membranes and/or skin tissue;

(b) and for the sterilisation of surgical instruments and other medical apparatus and equipment, for example respirators, ventilators, incubators, humidifiers, etc.;

(c) for incorporation in toothpastes and mouthwashes for inhibiting the formation of dental plaque, and gingivitis;

(d) for the disinfection of hard surfaces, for example plant and equipment used in the food and drink industries, and floors and walls in the home, factories and hospitals;

(e) for the disinfection of textiles, for example blankets, overalls, bed-linen, etc.;

(f) for the control of microbiological slime in the pulp and paper industries;

(g) for the control of micro-organisms in swimming pools, cooling water, pasteuriser water, aqueous oil emulsions such as metal working fluids, and other circulating water systems; and (h) as plant bactericides and fungicides.

Compounds of the invention also possess useful antifungal activity against, for example, *Candida albicans* or *Trichophyton mentagrophytes*, and algicidal and anti-yeast activity.

According to a further feature of the invention there are provided antibacterial or antifungal compositions comprising a compound of the formula VIII wherein $R^1$, $R^2$, $R^3$, $R^4$, $R^6$, $R^7$ and X have the meanings stated above, or an acid-addition salt thereof, and an inert diluent or carrier therefor.

The antibacterial or antifungal compositions of the invention are prepared by conventional means using conventional excipients. They include, for example, aqueous solutions, for example concentrated aqueous solutions, sterile, ready-to-use aqueous solutions, aqueous dispersions, and emulsions, for example oil-in-water emulsions, for example aqueous gels, creams, ointments and pastes. Suitable excipients include, for example, conventional wetting agents, dispersing agents, emulsifying agents, gelling agents or thickening agents.

According to a further feature of the invention, there is provided a contraceptive method which comprises applying to sperm or the locus of sperm a spermicidal, sperm-immobilising or mucospissic amount of a compound of the invention of the formula V.

In one aspect of this method of the formula V, when applied to vaginal mucus at a suitable concentration, very rapidly increases its viscosity, to the extent that it becomes essentially impenetrable to sperm, and forms a physical barrier to conception in the same way as a rubber sheath or diaphragm cap.

Besides increasing the viscosity of vaginal mucus, when the mucus comes into contact with a bisbiguanide compound of the formula V, other changes occur in its intrinsic properties, such as its morphology, rheology and water uptake and visco-elastic properties, which can also effect its penetrability to sperm. The compounds also possess spermicidal or sperm-immobilising properties.

In vitro, the compounds of the formula V exert a useful contraceptive effect at concentrtions down to about $10^{-3}$ to $10^{-4}\%$, and a suitable amount to be applied to the human vagina for contraceptive purposes is from 1.0 g. to $10^{-4}$ g.

The compound of the formula V may be applied to the vagina in conventional manner, for example as a pessary, cream, liquid douche, gel, aerosol foam or impregnated tampon, or in a controlled delivery device of the compound in a polymer matrix.

According to a further feature of the invention there is provided a compound of the formula V, or a composition thereof, for use as a contraceptive.

The invention is illustrated but not limited by the following Examples in which the temperatures are expressed in degrees Celsius:

EXAMPLE 1

A mixture of 3-(benzylthio)hexane-1,6-diamine dihydrochloride (0.62 g.), 1-butyl-3-cyanoguanidine (1.12 g.) and sulpholane (0.5 ml.) was stirred in a bath at 160° for 2 hours and then cooled. The mixture was dissolved in hot methanol (10 ml.) and the solution was filtered. The filtrate was added to acetone (200 ml.) with stirring, and the precipitated solid was collected, to give 3-(benzylthio)hexane-1,6-bis(5-butylbiguanide) dihydrochloride m.p. 134°-136°.

The 3-(benzylthio)hexane-1,6-diamine dihydrochloride used as starting material may be obtained as follows:

2-Hexenedinitrile (5.3 g.) was added to a mixture of phenylmethanethiol (6.82 g.), a 50% dispersion of sodium hydride in mineral oil (0.3 g.) and isopropanol (10 ml.) which was stirred under an atmosphere of argon. The mixture was refluxed for 2 hours and then cooled and treated with water (50 ml.). The mixture was extracted with ethyl acetate and the extract was dried and evaporated to dryness. The residue was dissolved in chloroform (50 ml.), the solution was stirred under an argon atmosphere while adding 1OM borane-dimethyl sulphide complex (10 ml.) and the mixture was then stirred at reflux under an argon atmosphere for 24 hours. The resulting gelatinous mass was cooled to room temperature, methanol (50 ml.) was added over 1 hour, and the mixture was stirred until a clear solution was obtained. The solution was acidified to pH 1 with concentrated hydrochloric acid and then evaporated to dryness. The residue was partitioned between water and diethyl ether, and the aqueous phase was separated, basified with 1ON aqueous sodium hydroxide and then extracted three times with ethyl acetate. The combined ethyl acetate extracts were dried and then evaporated to dryness. The residue was dissolved in acetonitrile, and the solution was acidified with a solution of hydrogen chloride in diethyl ether, to precipitate 3-(benzylthio)-hexane-1,6-diamine dihydrochloride, m.p. 178°-180°.

The 1-butyl-3-cyanoguanidine used as a starting material in the above process may be obtained by the general process described in the latter part of Examples 2-10.

EXAMPLES 2-10

The process described in the first part of Example 1 was repeated, using the appropriate 3-thio-substituted hexane-1,6-diamine dihydrochloride and the appropriate 1-substituted-cyanoguanidine, to prepare the following compounds:

| $R^1NH.C(:NH)NH.C(:NH)NH(CH_2)_2CH(YR^5)(CH_2)_3NH.C—$ | | |
|---|---|---|
| $(:NH)NH.C(:NH)NHR^3.2HCl$ | | |
| No | $R^1(=R^3)$ | $YR^5$ | Melting point °C. |
| 2 | isopropyl | benzylthio | 166-169 |
| 3 | cyclohexyl | benzylthio | 224-228 |
| 4 | benzyl | benzylthio | 119-121 |
| 5 | hexyl | benzylthio | 159-161 |
| 6 | butyl | phenylthio | 182-184 |
| 7 | cyclohexyl | phenylthio | 229-231 |
| 8 | benzyl | phenylthio | 170-172 |
| 9 | phenethyl | phenylthio | 144-147 |
| 10 | hexyl | phenylthio | 175-179 |

The 3-(phenylthio)hexane-1,6-diamine used as starting material in Examples 6 to 10 above may be prepared by the process described above for the manufacture of 3-(benzylthio)hexane-1,6-diamine, but using thiophenol in place of phenylmethanethiol. After crystallisation from a mixture of ethanol and acetonitrile it has m.p. 190°-191°.

The 3-cyano-1-hexylguanidine used as a starting material in Examples 5 and 10 above may be obtained as follows:

A mixture of hexylamine hydrochloride (63.5 g.), sodium dicyanamide (44.5 g.) and butanol (200 ml.) was heated at reflux for 18 hours and then cooled. The mixture was filtered and the filtrate was evaporated to dryness. The residue was stirred with water and the insoluble solid was collected and crystallised from aqueous ethanol to give 3-cyano-1-hexylguanidine (40 g.) m.p. 103°-105°.

The other 3-cyano-1-substituted-guanidines used as starting materials in Examples 1-4 and 6-9 are prepared similarly, using the appropriate amine in place of hexylamine.

EXAMPLES 11-17

The process described in Example 1 was repeated, using the appropriate 1-substituted-3-cyanoguanidine, and the appropriate 2-substituted pentane-1,5-diamine in place of 3-(benzylthio)hexane-1,6-diamine, to produce the following compound:

| $R^1NH.C(:NH)NH.C(:NH)NHCH_2CH(CH_2YR^5)(CH_2)_3NH—$ | | | |
|---|---|---|---|
| $C(:NH)NH.C(:NH)NHR^3.2HCl$ | | | |
| No | $R^1(=R^3)$ | $YR^5$ | Crystallisation solvent | Melting point °C. |
| 11 | cyclohexyl | benzyloxy | water | 218-220 |
| 12 | benzyl | benzyloxy | a | 136-138 (d) |
| 13 | phenethyl | benzyloxy | b | 113 (d) |
| 14 | hexyl | benzyloxy | water | 136-138 |
| 15 | cyclohexyl | phenylthio | a | 215-218 (d) |
| 16 | benzyl | phenylthio | c | 123-125 (d) |
| 17 | phenethyl | phenylthio | a | 152-154 (d) | a - methanol/acetone
b - methanol/ethyl acetate
c - methanol/acetonitrile
(d) - sulpholane omitted.

The 2-(benzyloxymethyl)pentane-1,5-diamine, used as starting material in Examples 11-14, may be obtained as follows:

A 50% dispersion of sodium hydride in mineral oil (200 mg.) was added to benzyl alcohol (32.4 g.) and the mixture was stirred until effervescence had ceased. The solution was treated with 2-methyleneglutaronitrile (15.9 g.) and the mixture was kept at room temperature for 24 hours. The reaction mixture was diluted with diethyl ether and the solution was washed three times with water, and then dried and evaporated to dryness to give 2-(benzyloxymethyl)glutaronitrile (32 g.). The crude 2-(benzyloxymethyl)glutaronitrile was reduced with borane-dimethyl sulphide complex in a similar process to that described in Example 1 to give 2-(benzyloxymethyl)pentane-1,5-diamine dihydrochloride, m.p. 159°-161° (after crystallisation from ethanol).

EXAMPLE 18

An intimate mixture of propylamine hydrochloride (1.15 g.) and 2-(phenylthiomethyl)pentane-1,5-bis(3-cyanoguanidine) (0.54 g.) was heated at 150° (bath temperature) for 2 hours. The cooled reaction mixture was shaken with a mixture of methylene chloride (30 ml.) and water (30 ml.). The organic and aqueous phases were decanted from the insoluble gummy material and the gum was washed again with methylene chloride and water. The insoluble gum crystallised from a mixture of methanol and acetonitrile to give 2-(phenylthiomethyl)pentane-1,5-bis(5-propylbiguanide) dihydrochloride, m.p. 136°-137°.

The 2-(phenylthiomethyl)pentane-1,5-bis(3-cyanoguanidine) used in the above preparation may be obtained as follows:

A mixture of thiophenol (3.63 g.), 2N aqueous sodium hydroxide (25 ml.) and 2-methyleneglutaronitrile (3.2 g.) was stirred at room temperature for 18 hours. The mixture was extracted with diethyl ether, and the ether extract washed with water and then dried and evaporated to dryness to give 2-(phenylthiomethyl)glutaronitrile which was used without further purification.

A solution of 2-(phenylthiomethyl)glutaronitrile (3.0 g.) in tetrahydrofuran (30 ml.) was stirred under an argon atmosphere while adding 10M borane-dimethyl sulphide complex (3 ml.), and the mixture was stirred at room temperature for 48 hours. The resulting gelatinous mass was treated with methanol (50 ml.) added over 1 hour and the mixture was stirred until a clear solution was obtained. The solution was acidified with a solution of hydrogen chloride in diethyl ether and then evaporated to dryness. The residue was partitioned between water and diethyl ether, and the aqueous phase was basified with 10N aqueous sodium hydroxide and then extracted three times with ether. The combined ether extracts were dried and then evaporated to dryness. The residue was purified by column chromatography on silica gel (150 g.) eluting with a mixture of ethyl acetate/methanol/concentrated ammonia, 6:1:0.5 (v/v) to give 2-(phenylthiomethyl)pentane-1,5-diamine characterised as the dihydrochloride, m.p. 166°-169°, after crystallisation from ethanol.

A mixture of sodium dicyanamide (1.8 g.), 2-(phenylthiomethyl)pentane-1,5-diamine dihydrochloride (2.0 g.) and butanol (20 ml.) was refluxed for 18 hour. The hot solution was filtered and the filtrate was evaporated to dryness. The residue was purified by column chromatography on silica gel (150 g.), eluting with 5% v/v methanol in ethyl acetate, to give 2-(phenylthiomethyl)- pentane-1,5-bis(3-cyanoguanidine) as a gum which was used without further purification.

EXAMPLES 19–24

The process described in Example 1 was repeated, using the appropriate substituted diamine and the appropriate cyanoguanidine as starting materials, but omitting the sulpholane, to manufacture the following compounds:

| | | R$^1$R$^2$N.C(:NH)NH.C(:NH)NH(CH$_2$)$_2$CH[5(CH$_2$)$_n$CH$_3$]—(CH$_2$)$_3$NH.C(:NH)NH.C(:NH)NR$^3$R$^4$.2HCl | | | |
|---|---|---|---|---|---|
| Ex. | R$^1$(=R$^3$) | R$^2$(=R$^4$) | n | Crystallisation solvent | m.p. |
| 19 | ethyl | H | 11 | a | 172–173 |
| 20 | methyl | H | 9 | a | 86–88 |
| 21 | ethyl | H | 9 | b | 164–166 |
| 22 | isopropyl | H | 9 | b | 202–204 |
| 23 | methyl | methyl | 9 | a | 172–175 |
| 24 | ethyl | ethyl | 9 | a | 178–179 | a – purified by medium pressure liquid chromatography (MPLC) on Merck Lichoprep RP-18 eluting with aqueous methanol
b – isopropanol-acetone.

The diamines used as starting materials in the above Examples 19–24 were obtained in the same manner as 2-(phenylthiomethyl)pentane-1,5-diamine, described in the second part of Example 18, but starting with the appropriate alkyl thiol in place of thiophenol. There were thus prepared:
2-(dodecylthiomethyl)pentane-1,5-diamine dihydrochloride, m.p. 312°–316°; and
2-(decylthiomethyl)pentane-1,5-diamine dihydrochloride, m.p. 198°–225°, used without further purificaiton.

EXAMPLES 25–30

The process described in Example 18 was repeated, using the appropriate amine and the appropriate bis(cyanoguanidine) as starting materials, to manufacture the following compounds:

| | | R$^1$R$^2$N.C(:NH)NH.C(:NH)NH(CH$_2$)$_2$CH[Y(CH$_2$)$_n$CH$_3$]—(CH$_2$)$_3$NH.C(:NH)NH.C(:NH)NR$^3$R$^4$.2HCl | | | | |
|---|---|---|---|---|---|---|
| Ex | R$^1$(=R$^3$) | R$^2$(=R$^4$) | Y | n | Crystallisation solvent | m.p. |
| 25 | ethyl | H | O | 11 | a | 153 |
| 26 | methyl | methyl | O | 11 | a | 160–162 |
| 27 | H | H | S | 7 | a | 149–152 |
| 28 | methyl | H | S | 7 | a | 70–76 |
| 29 | ethyl | H | S | 7 | b | 154–157 |
| 30 | isopropyl | H | S | 7 | a | 204–207 | a – purified by MPLC on Merck Lichoprep RP-18 eluting with aqueous methanol
b – isopropanol-acetone.

The 2-(dodecyloxymethyl)pentane-1,5-bis (3-cyanoguanidine, used as the starting material in Examples 25 and 26, was manufactured as follows:

Crude 2-(dodecyloxymethyl)pentane-1,5-diamine dihydrochloride (20 g.) and sodium dicyanamide (10.4 g.) were dissolved in butanol (150 ml.) and heated under reflux for 4 hours. The mixture was allowed to cool and was then filtered through celite (kieselguhr). The filtrate was concentrated under reduced pressure to give an oil, which was chromatographed on silica gel (500 g.) using a gradient elution starting at isopropanol-methylene chloride (1:9 by volume) and finishing at isopropanol-methylene chloride (1:4 by volume). The product, [R$_f$=0.5 on thin layer chromatography on silica, using isopropanol-methylene dichloride (1:3 by volume) and visualizing with chloroplatinate spray reagent] 2-(dodecyloxymethylene)pentane-1,5-bis(3-cyanoguanidine) was obtained as a colourless oil, on evaporation of the appropriate fractions from the gradient chromatography, which was crystallised from acetonitrile, m.p. 100°–102°.

In a similar manner, starting from 2-(octylthiomethyl)pentane-1,5-diamine dihydrochloride, there was obtained 2-(octylthiomethylene)pentane-1,5-bis(3-cyanoguanidine).

What we claim is:
1. A bisguanide compound of the formula:

R$^1$R$^2$N.C(:NR$^6$)NH.C(:NH)NH.CH$_2$X—(CH$_2$)$_3$N-
H.C(:NH)NH.C(:NR$^7$)NR$^3$R$^4$      V or a tautomer thereof, wherein R$^1$, R$^2$, R$^3$ and R$^4$ which may be the same or different, are each hydrogen, a 1–16C alkyl radical, a 2–16C alkoxyalkyl radical, a 3–12C cycloalkyl radical, a (3–12C cycloalkyl)-(1–4C alkyl) radical, or an optionally substituted phenyl or phenyl(1–4C alkyl) radical, or R$^1$ and R$^2$ and the nitrogen atom to which they are attached, or R$^3$ and R$^4$ and the nitrogen atom to which they are attached, which may be the same or different, are each a 1-azetidinyl, 1-pyrrolidinyl, piperidiono, hexamethyleneimino, heptamethyleneimino, morpholino or 4-(1–8C alkanoyl)-1-piperazinyl radical each of which may bear 1–3C alkyl substituents; each of R$^6$ and R$^7$, which may be the same or different, is hydrogen or a 1–8C alkyl radical; and X is an ethylene or ethylidene radical of the formula:

—CH$_2$CH(YR$^5$)—      VI or

—CH(CH$_2$YR$^5$)—      VII reading from left to right in formula V above, wherein Y is an oxgyen or sulphur atom and R$^5$ is a 1–16C alkyl, 3–12C cycloalkyl, (3–12C cycloalkyl)-(1–4C alkyl), optionally substituted phenyl or optionally substituted phenyl(1–4C alkyl) radical, wherein when any of R$^1$, R$^2$, R$^3$, R$^4$ and R$^5$ is or contains a substituted phenyl radical, the substituents(s) thereon are selected from the group consisting of halogen atoms and amino, carbamoyl, cyano, hydroxy, nitro and trifluoromethyl radicals, 1–6C alkyl, alkoxy, alkanoyl, alkylaminio and alkanoylamino radicals and 2–6C alkoxycarbonyl and dialkylamino radicals and the acid addition salts thereof.

2. A compound as claimed in claim 1 wherein each of R$^1$, R$^2$, R$^3$ and R$^4$ which may be the same or different, is hydrogen or a methyl, ethyl, n-propyl, isopropyl, n-butyl, isobutyl, sec-butyl, tert-butyl, pentyl, neopentyl, octyl, 2-ethylhexyl, dodecyl, hexadecyl, cyclobutyl, cyclopentyl, cyclohexyl, cycloheptyl, cyclopentylmethyl, cyclohexylmethyl, or a phenyl, benzyl, α-methylbenzyl, α-ethylbenzyl or phenylethyl radical each optionally substituted in the phenyl ring thereof by chlorine, bromine, iodine or fluorine atoms, or by amino, carbamoyl, cyano, hydroxy, nitro, trifluoromethyl, methyl, ethyl, propyl, butyl, pentyl, hexyl, methoxy, ethoxy, propoxy, acetamido, propionamido, butyramido, methylamino, ethylamino, propylamino, acetyl, propionyl, butyryl, methoxycarbonyl, ethoxycarbonyl, dimethylamino, diethylamino, 2-methoxyethyl, 3-dodecyloxypropyl, 6-hexyloxyhexyl, 2-tetradecyloxyethyl or 15-methoxypentadecyl radical; or $R^1$ and $R^2$, or $R^3$ and $R^4$, together with the nitrogen atom to which they are attached, which may be the same or different, form a 1-pyrrolidinyl or piperidino radical; $R^5$ has any of the meanings given above for $R^1$, $R^2$, $R^3$ or $R^4$ except hydrogen, and each of $R^6$ and $R^7$ which may be the same or different, is hydrogen or a methyl, ethyl, n-propyl, isopropyl, n-butyl, isobutyl, sec-butyl, tert-butyl, pentyl, neopentyl or octyl radical.

3. A compound as claimed in claim 2 wherein each of $R^1$, $R^2$, $R^3$, $R^4$ and $R^5$ which may be the same or different, is a phenyl, benzyl, α-methylbenzyl, α-ethylbenzyl, phenethyl, 2-, 3- or 4-chlorophenyl, 2-, 3- or 4-bromophenyl, 2-, 3- or 4- fluorophenyl, 2,3-, 2,4-, 2,5-, 2,6-, 3,4- or 3,5-dichlorophenyl, 2-chloro-3-fluorophenyl, 2-, 3- or 4-methylphenyl, 2,3-, 2,4-, 2,5-, 2,6-, 3,4- or 3,5-dimethylphenyl, 2-, 3- or 4-methoxyphenyl, 2-, 3- or 4-acetylphenyl, 2-, 3- or 4-methylaminophenyl, 2-, 3- or 4-acetamidophenyl, 2-, 3- or 4-methoxycarbonylphenyl, 2-, 3- or 4-dimethylaminophenyl, 2-, 3- or 4-nitrophenyl, 2-, 3- or 4-chlorobenzyl, 2-, 3- or 4-bromobenzyl, 2-, 3- or 4-fluorobenzyl, 2,3-, 2,4-, 2,5-, 2,6-, 3,4- or 3,5-dichlorobenzyl, 2-chloro-4-fluorobenzyl, 2-, 3- or 4-methylbenzyl, 2,3-, 2,4-, 2,5-, 2,6-, 3,4- or 3,5-dimethylbenzyl, 2-, 3- or 4-methoxybenzyl, 2-, 3- or 4-acetylbenzyl, 2-, 3- or 4-methylaminobenzyl, 2-, 3- or 4-acetamidobenzyl, 2-, 3- or 4-methoxycarbonylbenzyl, 2-, 3- or 4-dimethylaminobenzyl, 2-, 3- or 4-nitrobenzyl, 2-, 3- or 4-chloro-α-methylbenzyl, 2-, 3- or 4-chlorophenethyl or bis(2-, 3- or 4-chlorophenyl)methyl radical.

4. A compound as claimed in claim 1 which is in the form of a salt with hydrochloric, hydrobromic, phosphoric, sulphuric, acetic, D-gluconic, 2-pyrrolidone-5-carboxylic, methanesulphonic, carbonic, lactic or glutamic acid.

5. A compound as claimed in claim 1 which is 2-(benzyloxymethyl)pentane-1,5-bis(5-hexylbiguanide), 2-(phenylthiomethyl)pentane-1,5-bis(5-phenethylbiguanide), 2-(decylthiomethyl)pentane-1,5-bis(5-isopropylbiguanide), 2-(decylthiomethyl)pentane-1,5-bis- (5,5-diethylbiguanide), 3-(phenylthio)hexane-1,6-bis-(5-hexylbiguanide), 3-(phenylthio)hexane-1,6-bis(5-cyclohexylbiguanide), 3-(benzylthio)hexane-1,6-bis(5-hexylbiguanide) and 3-(benzylthio)hexane-1,6-bis(5-cyclohexylbiguanide) or a dihydrochloride thereof.

* * * * *